United States Patent
Guo

(10) Patent No.: US 6,572,889 B1
(45) Date of Patent: Jun. 3, 2003

(54) CONTROLLED RELEASE SOLID DOSAGE CARBAMAZEPINE FORMULATIONS

(75) Inventor: Jian-Hwa Guo, Hudson, OH (US)

(73) Assignee: Noveon IP Holdings Corp., Cleveland, OH (US)

( * ) Notice: Subject to any disclaimer, the term of this patent is extended or adjusted under 35 U.S.C. 154(b) by 0 days.

(21) Appl. No.: 10/092,826

(22) Filed: Mar. 7, 2002

(51) Int. Cl.$^7$ .............. A61K 9/22; A61K 9/26; A61K 9/52
(52) U.S. Cl. ............ 424/468; 424/465; 424/452; 424/469; 424/486; 424/487
(58) Field of Search ............... 424/464, 465, 424/458, 468, 487, 489, 469, 486

(56) References Cited

U.S. PATENT DOCUMENTS

| | | | |
|---|---|---|---|
| 4,857,336 A | | 8/1989 | Khanna et al. .............. 424/473 |
| 5,326,570 A | * | 7/1994 | Rudnic et al. .............. 424/450 |
| RE34,990 E | | 7/1995 | Khanna et al. .............. 424/473 |
| 5,773,025 A | * | 6/1998 | Baichwal .................... 424/458 |
| 5,840,329 A | * | 11/1998 | Bai ............................. 424/458 |
| 5,912,013 A | * | 6/1999 | Rudnic et al. .............. 424/465 |
| 5,980,942 A | * | 11/1999 | Katzhendler et al. ....... 424/465 |
| 6,039,980 A | * | 3/2000 | Baichwal .................... 424/500 |
| 6,048,547 A | * | 4/2000 | Seth et al. .................. 424/464 |
| 6,284,803 B1 | | 9/2001 | Kothrade et al. .......... 514/772.1 |
| 6,294,201 B1 | | 9/2001 | Kettelhoit et al. .......... 424/473 |
| 6,296,873 B1 | * | 10/2001 | Katzhendler et al. ....... 424/465 |
| 6,297,337 B1 | * | 10/2001 | Marchant et al. .......... 526/328 |
| 6,306,789 B1 | * | 10/2001 | Dettmar et al. ............ 424/487 |
| 6,312,728 B1 | | 11/2001 | Beiman et al. ............. 424/490 |
| 6,328,994 B1 | * | 12/2001 | Shimizu et al. ............ 424/489 |
| 6,338,857 B1 | * | 1/2002 | Seth ........................... 424/464 |
| 6,355,273 B1 | * | 3/2002 | Carli et al. ................. 424/489 |

* cited by examiner

Primary Examiner—Shep K. Rose
(74) Attorney, Agent, or Firm—Thoburn T. Dunlap; Hudak, Shunk & Farine Co., L.P.A.

(57) ABSTRACT

A polymer or copolymer composition derived from one or more unsaturated carboxylic acids that is cross-linked and carbamazepine in conjunction with conventional materials such as fillers, excipients, and surface active agents is disclosed. Solid dosage forms of immediate and sustained release tablets containing the polymer or copolymer composition can be formed by wet granulation or wet granulation followed by blending with direct compression ingredients. The polymer or copolymer, as a controlled release agent, can enhance controlled-release properties while meeting acceptable release rates as specified by the USP.

32 Claims, No Drawings

CONTROLLED RELEASE SOLID DOSAGE CARBAMAZEPINE FORMULATIONS

BACKGROUND OF THE INVENTION

1. Field of the Invention

The invention is directed to controlled release formulations of solid dosage carbamazepine utilizing a cross-linked polymer or copolymer derived from one or more unsaturated carboxylic acids, which provides controlled release properties at low concentrations, while meeting acceptable release rates as specified by the United States Pharmacopeial Convention (USP).

2. Description of the Prior Art

Carbamazepine is a well-known pharmaceutical agent for the clinical treatment of seizure disorders, including tonic-clonic (grand mal) seizures, complex partial seizures and trigeminal neuralgia. Currently, however, there are a limited number of oral therapeutic systems containing carbamazepine in solid dosage form.

In U.S. Pat. No. 4,857,336 and RE 34,990 to Khanna, et al, there is disclosed a therapeutic system for peroral administration of carbamazepine. The system comprises a wall made of a material permeable to water and impermeable to the components of the drug-containing core; a core containing finely particulate carbamazepine, a protective colloid, a swellable hydrophilic polymer and an optional water-soluble compound; and a passageway through the wall for delivering the core components to the environmental body fluid. The passageway is produced by mechanical or laser drilling of the outer wall.

A drug delivery system for the oral administration of carbamazepine and a method of treating a patient with the drug delivery systems is disclosed in U.S. Pat. No. 5,326,570. The drug delivery systems consist of an immediate release unit containing carbamazepine, a sustained release unit containing carbamazepine and an enteric release unit containing carbamazepine.

In U.S. Pat. No. 5,912,013 to Rudnic, et al, there is taught a composition for treating a patient with carbamazepine in a pharmaceutical dosage form which comprises a single dosage form containing multiple units within it capable of releasing their contents at varying times, i.e., a sustained release unit and an immediate release unit.

In U.S. Pat. No. 5,980,942, there is described a zero order sustained release matrix tablet formulation of carbamazepine. The matrix tablet formulation comprises a hydrophilic polymer gel which inhibits transformation of carbamazepine into carbamazepine dihydrate and effectively changes the anhydrous carbamazepine into an amorphous form which can be released from the matrix by zero-order release kinetics.

In U.S. Pat. No. 6,294,201 an osmotic drug release system for the oral administration of a pharmaceutical agent is disclosed. The osmotic drug delivery system consists of a shell and core containing a pharmaceutically active substance, xanthan and a vinyl pyrrolidone-vinyl acetate copolymer. These water-expandable polymers allow for the release of the active substance from the shell in a controlled manner.

These prior art methods of carbamazepine delivery, however, have the inherent drawbacks of being expensive and require time-consuming methods of production. Additionally, in order to achieve and maintain a therapeutic range, a higher concentration of carbamazepine is necessary.

SUMMARY OF THE INVENTION

Solid dosage forms of immediate and sustained release tablets containing carbamazepine are formed by wet granulation or by using granules formed by wet granulation mixed with direct compression ingredients. The solid dosage form consists of a polymer or copolymer derived from one or more unsaturated carboxylic acids that is cross-linked and carbamazepine in conjunction with conventional materials such as fillers, excipients, and surface active agents. The polymer or copolymer as a controlled release agent can enhance controlled-release properties at lower concentrations than prior art systems, while meeting acceptable release rates as specified by the USP.

DESCRIPTION OF THE PREFERRED EMBODIMENTS

The polymer or copolymers of the present invention provides immediate release or controlled release of carbamazepine in sustained release formulations, depending upon the choice of ingredients and processing of the formulation. The polymer or copolymers are derived from one or more unsaturated carboxylic acid monomers, (i.e., (di)carboxylic acid) generally having one or two carboxylic acid groups, desirably having one carbon to carbon double bond and containing generally a total of from 3 to about 10 carbon atoms and preferably from 3 to about 5 carbon atoms such as $\alpha$-$\beta$-unsaturated monocarboxylic acids, for example, acrylic acid, methacrylic acid, and crotonic acid, and the like, or dicarboxylic acids such as itaconic acid, fumaric acid, maleic acid, aconitic acid, and the like. Moreover, half ester monomers of such diacids with alkanols containing from 1 to about 4 carbon atoms can also be utilized, such as monomethyl fumarate. Preferred acids include acrylic acid or maleic acid. Additionally, diacids capable of forming cyclic anhydrides, such as maleic, may be polymerized as the anhydride and later reacted with water or alcohols to form the equivalent of maleic acid or monoalkyl maleate copolymer.

Optionally, one or more oxygen-containing unsaturated comonomers having a total of from 3 to about 40 carbon atoms, such as esters of the above unsaturated (di)carboxylic acids, that is, mono or di, especially alkyl esters containing a total of from 1 to about 30 carbon atoms in the alkyl group can also be utilized as comonomers to form the copolymer. Examples of such esters include ethyl acrylate, butyl acrylate, 2-ethylhexyl acrylate, dodecyl acrylate, hexadecyl acrylate, and octadecyl acrylate, and the like, with the $C_{10}$ to $C_{30}$ acrylates being preferred.

Another optional class of comonomers are the various anhydrides of the above-noted carboxylic acids such as maleic anhydride, and the like. Moreover, another optional class of suitable comonomers are the various alkyl vinyl ethers wherein the alkyl group contains from 1 to about 20 carbon atoms with examples including ethyl vinyl ether, methyl vinyl ether, and the like. Examples of suitable cross-linked commercially available rheology modifying polymers or copolymers include Carbopol® 941, 971 PNF, 981 and 71G manufactured by Noveon, Inc., as well as Synthalen L made by 3V/Sigma, Aqupec HV-501 and HG 501E made by Sumitomo Seika.

The amount of the one or more oxygen-containing acid comonomers when utilized is generally a minor amount, such as from about 0.01% to about 40% by weight, desirably from about 0.5% to about 35% by weight, and preferably from about 1% to about 25% by weight based upon the total weight of all the rheology modifying polymer or copolymer forming monomers and comonomers. Thus, the amount of the one or more unsaturated (di)carboxylic acid monomers, half ester thereof, or combinations thereof, is generally from about 60% to about 99.99% by weight, desirably from about 65% to about 99.5% by weight, and preferably from about 75% to about 99% by weight based upon the total weight of all rheology modifying polymer or copolymer forming monomers or comonomers.

The various polymers or copolymers of the present invention are generally anhydrous. That is, they generally contain 5 parts by weight or less, desirably 3 parts or 2 parts by weight or less, and preferably 1 part or less by weight, and even nil, that is no parts by weight, of water per 100 parts by weight of the one or more rheology modifying polymers or copolymers.

It is an important aspect of the present invention that the polymer or copolymer be cross-linked with one or more polyunsaturated monomers or comonomers. Suitable cross-linking agents are known to the art and literature and generally include the various allyl ethers of sucrose or pentaerythritol, or derivatives thereof, or various polyols. Specific examples include diallylphthalate, divinyl glycol, divinyl benzene, allyl (meth)acrylate, ethylene glycol di(meth)acrylate, diallyl itaconate, diallyl fumarate, or diallyl maleate. Derivatives of castor oils or polyols such as esterified with an ethylenically unsaturated carboxylic acid and the like can be used. Preferred cross-linking agents include divinyl glycol, allyl ether of sucrose, allyl ether of pentaerythritol, diallylphthalate, and combinations thereof.

The amount of the cross-linking agent is from about 0.01 to about 2 parts by weight, desirably from about 0.02 to about 1.5 parts by weight, and preferably from about 0.03 to about 1 part by weight per 100 total parts by weight of the one or more rheology monomers or comonomers.

The rheology modifying polymers or copolymers of the present invention are produced by conventional methods known to the art and to the literature such as by dispersion or precipitation polymerization utilizing suitable organic solvents such as various hydrocarbons, esters, halogenated hydrocarbon compounds and the like, with specific examples including aromatic solvents such as benzene, or toluene; various cycloaliphatic solvents such as cyclohexane; various esters such as ethyl acetate and methyl formate, ethyl formate; various chlorinated hydrocarbons such as dichloromethane; and combinations thereof. Preferred solvents generally include benzene, methylene chloride, blends of ethyl acetate and cyclohexane, or ethyl acetate, and the like.

In addition to containing the rheology modifying polymer or copolymer and carbamazepine as active ingredient, the solid dosage formulation will contain various fillers, excipients, surfactants, and the like, as are known to those skilled in the art. The excipients are generally utilized to give a desirable slow release profile as well as other desirable attributes of a solid dosage tablet, including color, hardness, crushing strength, and low friability. Accordingly, such excipients can be one or more of fillers, binders, colorants, coating agents, slow release compounds, and the like.

In order to produce a flowable mixture which contains the cross-linked polymer or copolymer of the present invention, as well as the active ingredient, suitable excipients can include microcrystalline cellulose such as Avicel® PH101, Avicel PH102, Avicel PH200, Avicel PH301, and Avicel PH302 available from FMC Corporation, Vivapur 101, Vivapur 102 available from Rettenmaier and Sohne GMbH, Emcocel 50 M and Emcocel 90 M available from Penwest Company; dicalcium phosphate such as Elcema® available from Degussa; A-Tab®; DiTab® available from Rhodia; lactose monohydrate such as Flow-Lac® 100; Pharmatose® DCL11, Pharmatose DCL15, Pharmatose DCL21 available from DMC International; Tablettose® 80 available from Meggle; and tricalcium phosphate such as Tri-Tab®; Fast Flo Lactose from Foremost; and Prosolve® (Silicified MCC) from Penwest. The amount of one or more excipients utilized will generally be from about 1 to about 90 parts by weight, with from about 5 to about 60 parts by weight of the total dosage formulation being preferred, based upon tablet performance. Higher levels of excipient are generally used with highly active drugs or where only a low dose of drug is being dispensed. This enables the preparation of a tablet which can be easily picked up, handled, counted, etc. Tablets which are too small are difficult to pick up, are easily dropped and lost, and are otherwise inconvenient.

Further excipients utilized are those customarily used in tableting for the preparation of granulates, including binders, lubricants, glidants, dispersants, fillers and the like. Thus, it is possible to include conventional materials such as lactose, saccharose, sorbitol, mannitol, starch, cellulose, or magnesium stearate, in addition to the excipients listed hereinabove.

Owing to the difficulty in solubilizing carbamazepine, it is contemplated to utilize various solubility enhancers and surface active agents in the practice of the present invention. One class of solubility enhancers which have little surfactant activity is the polyethylene glycol series, such as PEG 600. Other useful types in this series range in molecular weight from 200 to 7,000,000. Suitable surface active agents and solubility enhancers include anionic surfactants such as sodium lauryl sulfate, sodium, potassium or magnesium n-dodecyl sulfate, n-tetradecylsulfate, n-hexadecyl sulfate, n-tetradecyloxyethyl sulfate, n-hexadecyloxyethyl sulfate or n-octadecyloxyethyl sulfate; or sodium, potassium or magnesium n-dodecanesulfonate; sodium, potassium or magnesium n-tetradecanesulfonate, n-hexadecanesulfonate or n-octadecanesulfonate, and the like.

Additional suitable surfactants are non-ionic surfactants of the fatty acid polyhydroxy alcohol ester type such as sorbitan monolaurate, sorbitan monooleate, sorbitan monostearate or sorbitan monopalmitate, sorbitan tristearate or trioleate, polyethylene glycol fatty acid ester such as polyoxyethyl stearate, polyethylene glycol 600 stearate, and the like. Further additional surfactants include polyoxyethylene alkyl ethers, polyoxyethylene castor oil derivatives, sorbitan polyoxyethylene fatty acid esters, polyoxyethylene fatty acid esters, and polyoxyethylene stearates, such as defined in "Handbook of Pharmaceutical Excipients," (American Pharmaceutical Association Pub.; $3^{rd}$ Ed., 2000). A preferred surface active agent is sodium lauryl sulfate which is generally present in an amount from about 0.1 to about 10 parts by weight, and preferably from about 1 to about 5 parts by weight per 100 parts by weight of the total dosage formulation.

The polymers or copolymers may be utilized in combination with the active ingredient in either powder or granulated form. When in powder form, the powder mixture containing the active must be granulated to further process properly. Granulation can be accomplished by processes known to the art and in the literature, such as, for example, by roller compaction, by slugging, or utilizing wet methods such as a fluidized bed. Where the polymer is in granular form, it can either be incorporated with the active before granulation, or combined with the active or granules containing the active just before tableting or capsule filling. The granulated polymer or copolymer desirably has a specific particle size range so that when blended with the carbamazepine or granules containing carbamazepine, a flowable mixture is produced. This is so the mixture can either be tableted on a high-speed tablet press, or easily filled into capsules on automatic equipment. Desirably, the particle size of the polymer or copolymer powder will be from about 1 to about 20 microns, and preferably from about 2 to about 10 microns. Desirably, the particle size of the polymer or copolymer granules will be from about 74 to about 1,000 microns, and preferably from about 149 to about 425 microns.

The granulated cross-linked rheology modifying polymer or copolymers, carbamazepine, as well as the one or more excipients and surface active agents can be mixed in any conventional manner to produce a blend. For example, it can be mixed in a shell blender, a Vee blender, a double cone blender, a ribbon mixer, and the like. The polymer or copolymers of the present invention are suitable for producing solid dosage forms by generally all conventional processes, including granulation, grinding, compression, casting in a mold, tableting under pressure, and the like. However, preferred processes for production of the solid dosage form of the present invention are wet granulation and direct compression. In a wet granulation technique, the solid dosage form is prepared in the presence of either a granulation solvent or solution of a granulation binder, as is known in the art. The granulation binder may be the polymer or copolymer of the present invention, or any other polymer known to the art as a granulation binder, such as polyvinyl pyrrolidone, hydroxypropylmethyl cellulose, and the like. In a direct compression method, the mixture containing the polymer or copolymer and active is directly fed into any conventional tablet making machine wherein a desired amount of the mixture or blend is fed through an orifice or opening into a tablet die. The die is closed and compresses the mixture to produce a suitably sized and shaped solid dosage article such as a tablet. This method is more fully described in U.S. patent application Ser. No. 09/559,687, which is incorporated by reference herein.

The invention will be better understood by reference to the following examples which serve to illustrate but not to limit the present invention.

Example of Preparation of Solid Dosage Form by Wer Granulation

| Ingredients | Source | % w/w | Actual Weight (g) |
|---|---|---|---|
| Carbamazepine | Noveon | 65.0 | 650 |
| PEG 600 | Union Carbide | 8.0 | 8 |
| Kollidon ® CL | BASF | 23.0 | 230 |
| Carbopol 971P | Noveon | 3.0 | 30 |
| Talc | Aldrich | 0.5 | 5 |
| Mg Stearate | Synpro | 0.5 | 5 |

Anhydrous carbamazepine is weighed and placed in an Erweka Planetary Mixer. While operating the mixer at a speed of 150 rpm, polyethylene glycol (PEG) is slowly added and mixed for approximately 10 minutes. The remaining formulation ingredients except the magnesium stearate are combined with this mixture and mixed for an additional 5 minutes at 140 rpm. Deionized water is then added to the formulation in 20 milliliter (ml) increments every 2 minutes and the mixing speed is increased by 10 rpm, up to a maximum of 270 rpm, after the water additions. The endpoint is determined by observing the appearance of the granulation and by hand-squeezing a handful of the granulation and observing its compaction and cohesion behavior upon this treatment, a technique well known to those skilled in the art.

The wet granulation particles are removed from the mixer and passed through a US Standard #6 mesh. The sized particles are laid out on an aluminum baking tray in a thin layer not to exceed 0.25" thick and placed in a Blue-M Circulated Air Oven Model OV-55C-2 and dried for at least 8 hours at 60° C. In order to ensure removal of all water from the granules, the granules are removed from the oven, cooled, weighed, and dried further in the oven for an additional hour, followed by cooling and weighing a second time. This process is repeated until there is no weight loss between dryings.

Following drying, the granules are ground through a sieve stack to the desired particle size. For a 20 mesh particle size, a sieve stack of 8 mesh, 14 mesh, and 20 mesh was utilized. For a 14 mesh particle size, a sieve stack of 8 mesh and 14 mesh was utilized.

Magnesium stearate was then added to the formulation following sizing of the particles. To a Patterson-Kelly Twin Shell Mixer was added 95.5 grams (g) of each particle size together with 0.5 g of magnesium stearate. The mixture was then mixed for 2 minutes. After checking the flow index, the mixture was then either tableted or made into capsules.

Example of Dosage Form Prepared by Mixing Wet Granulation Granules with Direct Compression Ingredients

| Ingredients | Source | % w/w | Actual wt. (g) |
|---|---|---|---|
| Granules of Example 1 | Noveon | 60 | 12 |
| Granulated Lactose | Foremost | 20 | 4 |
| Carbopol 71G Polymer | Noveon | 15 | 3 |
| Sodium lauryl sulfate | Fisher | 5 | 1 |

Preparation of wet granulation granules is as described in Example 1. The appropriate weights of the wet granulation granules were mixed with the direct compression ingredients in a Patterson-Kelly Twin Shell Mixer and mixed for 25 minutes. The wet granulation/direct compression mixture was then either tableted or made into capsules.

Dissolution Testing

USP requirements for dissolution rates of carbamazepine are as follows:

| Time (minutes) | Amount Dissolved |
|---|---|
| 180 | Between 10% and 35% |
| 360 | Between 35% and 65% |
| 720 | Between 65% and 90% |
| 1440 | Not less than 75% |

Each dissolution test was performed in accordance to the USP method for Carbamazepine Extended-Release Tablets (Apparatus 1, 1000 RPM, 900 mL water). A Hanson SR-8 unit was used to run the tests, and six capsules were tested during each run. A sample was taken from each of the 6 vessels every 15 minutes for 24 hours and directly scanned using a Perkin-Elmer UV/VIS model Lambda 2. The data was collected using Perkin-Elmer Dissolution Software.

TABLE 1

(Wet Granulation - Capsules)

| Time (minutes) | 180 | 360 | 720 | 1440 |
|---|---|---|---|---|
| % Dissolved | 32.03 | 46.71 | 64.04 | 75.7 |
| Std Deviation | 2.8 | 2.32 | 1.82 | 1.41 |

TABLE 2

(Wet Granulation granules with Direct Compression Ingredients - Capsules)

| Time (minutes) | 180 | 360 | 720 | 1440 |
|---|---|---|---|---|
| % Dissolved | 32.93 | 48.2 | 65.19 | 77.65 |
| Std. Deviation | 3.66 | 1.74 | 3.2 | 4.96 |

The above results clearly indicate that the solid dosage form of the present invention meets the USP criteria for dissolution rates of extended release carbamazepine.

While in accordance with the Patent Statutes the best mode and preferred embodiment have been set forth, the scope of the invention is not limited thereto but rather by the scope of the claims.

What is claimed is:

1. A controlled release solid dosage carbamazepine composition, comprising:

a rheology modifying copolymer composition derived from one unsaturated (d)carboxylic acid monomer having a total of from 3 to about 10 carbon atoms, or at least one half ester monomer of said unsaturated dicarboxylic acid with an alkanol having from 1 to about 4 carbon atoms, or combinations thereof, and optionally one or more oxygen-containing comonomers having from 3 to about 40 carbon atoms;

a cross-linking agent;

carbamazepine as an active ingredient, wherein said carbamazepine is in anhydrous form;

one or more excipients; and optionally, one or more surface active agents.

2. A composition according to claim 1, including from about 0.5% to about 40.5% by weight of said one or more oxygen containing unsaturated comonomers in an amount from about 0.5% to about 40.5% by weight based upon the total weight of said rheology modifying polymer or copolymer forming monomers and comonomers, wherein said oxygen containing comonomers comprise an anhydride of said unsaturated (di)carboxylic acid, or an alkyl ester of said unsaturated carboxylic acid wherein said alkyl group has from 1 to about 30 carbon atoms, or an alkyl vinyl ether wherein said alkyl group has from 1 to about 20 carbon atoms, or combinations thereof.

3. A composition according to claim 2, wherein said unsaturated (di)carboxylic acid has from 3 to about 5 carbon atoms, and wherein the amount of said unsaturated (di) carboxylic acid monomer or said half ester monomer or combination thereof is from about 60 to about 99.99 percent by weight based upon the total weight of all rheology modifying polymer or copolymer forming monomers and comonomers.

4. A composition according to claim 3, wherein said cross-linking agent is an allyl ether of sucrose or pentaerythritol, or a derivative thereof, a polyalcohol, divinyl glycol, diallylphthalate, divinyl benzene, allyl (meth) acrylate, ethylene glycol di(meth)acrylate, diallyl itaconate, diallyl fumarate, diallyl maleate, castor oil or a polyol esterified with an ethylenically unsaturated carboxylic acid, or combinations thereof.

5. A composition according to claim 4, wherein said polymer or copolymer is derived from acrylic acid or maleic acid, or combinations thereof, wherein said cross-linking agent is divinyl glycol, an allyl ether of sucrose, an allyl ether of pentaerythritol, diallylphthalate, or combinations thereof, and wherein the amount of said cross-linking agent is from about 0.03 to about 1.0 part by weight per 100 parts by weight of all of said monomers or comonomers.

6. A composition according to claim 2, wherein the amount of said one or more oxygen-containing comonomers when utilized is from about 1 to about 25 percent by weight based upon the total weight of all of said rheology modifying polymer or copolymer forming monomers and comonomers.

7. A composition according to claim 5, wherein said excipients are one or more of microcrystalline cellulose, dicalcium phosphate, lactose monohydrate, tricalcium phosphate, lactose, sacchrose, sorbitol, mannitol, starch, cellulose, cellulose derivatives, or magnesium stearate, or combinations thereof, and said excipients are present in an amount from about 1 to about 90 parts by weight per 100 parts by weight of said total dosage composition.

8. A composition according to claim 7, wherein said excipient is lactose monohydrate or magnesium stearate and said excipient is present in an amount from about 1 to about 90 parts by weight per 100 parts by weight of said total dosage composition.

9. A composition according to claim 1, further including said surface active agent, and wherein said surface active agent is one or more of sodium lauryl sulfate, sodium, potassium or magnesium n-dodecyl sulfate, n-tetradecylsulfate, n-hexadecyl sulfate, n-tetradecyloxyethyl sulfate, n-hexadecyloxyehtyl sulfate or n-octadecyloxyethyl sulfate; or sodium, potassium or magnesium n-dodecanesulfonate, e.g. sodium, potassium or magnesium n-tetradecanesulfonate, n-hexadecanesulfonate or n-octadecanesulfonate, sorbitan monolaurate, sorbitan monooleate, sorbitan monostearate or sorbitan monopalmitate, sorbitan tri-stearate or trioleate, polyethylene glycol fatty acid ester such as polyoxyethyl stearate, polyoxyethylene alkyl ethers, polyoxyethylene castor oil derivatives, sorbitan polyoxyethylene fatty acid esters, polyethylene glycol stearate, and said surface active agent is present in an amount from about 0.1 to about 10 parts by weight per 100 parts by weight of said total dosage composition.

10. A composition according to claim 9, wherein said surface active agent is sodium lauryl sulfate or polyethylene glycol stearate, and said surface active agent is present in an amount from about 1 to about 5 parts by weight per 100 parts by weight of said total dosage composition.

11. A composition according to claim 1, wherein said polymer or copolymer is derived from acrylic acid or maleic acid, or combinations thereof, wherein said cross-linking agent is divinyl glycol, an allyl ether of sucrose, an allyl ether of pentaerythritol, or diallylphthalate, wherein said excipient is magnesium stearate or lactose monohydrate, or combinations thereof, and wherein said surface active agent is sodium lauryl sulfate or polyethylene glycol 600 stearate, or combinations thereof.

12. A composition according to claim 1, wherein said composition is in tablet form.

13. A composition according to claim 12, wherein said tablet is formed by direct compression.

14. A composition according to claim 11, wherein said composition is in tablet form.

15. A composition according to claim 14, wherein said tablet is formed by direct compression.

16. A composition according to claim 1, wherein said composition is in capsule form.

17. A composition according to claim 11, wherein said composition is in capsule form.

18. A process for preparing a controlled release solid dosage carbamazepine composition comprising the steps of:
   a. forming a mixture comprising one unsaturated (d)carboxylic acid monomer having a total of from 3 to about 10 carbon atoms, or at least one half ester monomer of said unsaturated dicarboxylic acid with an alkanol having from 1 to about 4 carbon atoms, or combinations thereof, and optionally one or more oxygen-containing comonomers having from 3 to about 40 carbon atoms, a cross-linking agent;
   b. polymerizing said mixture to form a rheology modifying polymer or copolymer;
   c. adding an active ingredient comprising carbamazepine in anhydrous form, one or more excipients, and one or more surface active agents to said polymer or copolymer; and
   d. forming a solid dosage article therefrom.

19. A process according to claim 18, wherein said unsaturated (di)carboxylic acid monomer has from about 3 to about 5 carbon atoms, and wherein the amount of said unsaturated (di)carboxylic acid monomer is from about 60% to about 99.99% by weight based upon the total weight of all of said rheology modifying polymer or copolymer forming monomers or comonomers.

20. A process according to claim 18, wherein said cross-linking agents is an allyl ether of sucrose or pentaerythritol, or a derivative thereof, a polyalcohol, diallylphthalate, divinyl glycol, divinyl benzene, allyl (meth)acrylate, ethylene glycol di(meth)acrylate, diallyl itaconate, diallyl sumarate, diallyl maleate, castor oil or a polyol esterifaed with an ethylenically unsaturated carboxylic acid, or combinations thereof.

21. A process according to claim 19, wherein said unsaturated carboxylic acid monomer is acrylic acid or methacyrlic acid, and wherein said cross-linking agent is an allyl ether of sucrose, an allyl ether of pentaerythritol, trimethylolpropane allyl ether, trimethoxypropylallyl ether, divinyl glycol, or combinations thereof and wherein said cross-linking agent is present in an amount from about 0.01 to about 5 parts by weight per 100 parts by weight of all of said monomers.

22. A process according to claim 21, wherein said excipients are one or more of microcrystalline cellulose, dicalcium phosphate, lactose monohydrate, tricalcium phosphate, lactose, saccharose, sorbitol, mannitol, starch, cellulose, or magnesium stearate, or combinations thereof, and said excipients are present in an amount from about 1 to about 90 parts by weight per 100 parts by weight of said total dosage composition.

23. A process according to claim 22, wherein said excipient is lactose monohydrate or magnesium stearate and said excipient is present in an amount form about 1 to about 90 parts by weight per 100 parts by weight of said total dosage composition.

24. A process according to claim 22, wherein said surface active agent is one or more of sodium lauryl sulfate, sodium monoglycerate; sodium, potassium or magnesium n-dodecyl sulfate, n-tetradecylsulfate, n-hexadecyl sulfate, n-tetradecyloxyethyl sulfate, n-hexadecyloxyethyl sulfate or n-octadecyloxyethyl sulfate; or sodium, potassium or magnesium n-dodecanesulfonate, sodium, potassium or magnesium n-tetradecanesulfonate, n-hexadecanesulfonate or n-octadecanesulfonate, sorbitan monolaurate, sorbitan monooleate, sorbitan monostearate or sorbitan monopalmitate, sorbitan tri-stearate or trioleate, polyoxyethylene alkyl ether, polyoxyethylene castor oil derivative, sorbitan polyoxyethylene fatty acid ester, polyethylene glycol fatty acid ester such as polyoxyethyl stearate, polyethylene glycol stearate, and said surface active agent is present in an amount from about 0.1 to about 10 parts by weight per 100 parts by weight of the total dosage composition.

25. A process according to claim 24, wherein said surface active agent is sodium lauryl sulfate or polyethylene glycol stearate, and said surface active agent is present in an amount from about 1 to about 5 parts by weight per 100 parts by weight of the total dosage composition.

26. The process of claim 18, wherein said solid dosage article is formed by one or more of wet granulation and direct compression.

27. The process of claim 26, wherein said solid dosage article is a capsule.

28. The process of claim 26 wherein said solid dosage article is a tablet.

29. The process of claim 20, wherein said solid dosage article is formed by wet granulation.

30. The process of claim 23, wherein said solid dosage article is formed by wet granulation.

31. The process of claim 20, wherein said solid dosage article is formed by direct compression.

32. The process of claim 23, wherein said solid dosage article is formed by direct compression.

\* \* \* \* \*